United States Patent [19]
Leonardi

[11] Patent Number: 5,495,623
[45] Date of Patent: Mar. 5, 1996

[54] SPORTS PAD FOR EYEWEAR FRAMES

[75] Inventor: Peter F. Leonardi, Gloversville, N.Y.

[73] Assignee: Halo Sports and Safety, Inc., Gloversville, N.Y.

[21] Appl. No.: 195,468

[22] Filed: Feb. 14, 1994

[51] Int. Cl.6 ........................................... A61F 9/02
[52] U.S. Cl. ..................... 2/431; 2/439; 2/440
[58] Field of Search ........................... 2/431, 439, 440, 2/428, 430, 454

[56] References Cited

U.S. PATENT DOCUMENTS

| | | | |
|---|---|---|---|
| 1,288,140 | 12/1918 | Nixson | 2/439 |
| 1,306,357 | 6/1919 | Shindel | 2/439 |
| 1,344,474 | 6/1920 | Beattey . | |
| 1,754,694 | 4/1930 | Neuwirth | 2/440 |
| 2,406,608 | 8/1946 | Joyce | 2/450 |
| 2,504,524 | 4/1950 | Hayward | 2/452 |
| 2,545,428 | 3/1951 | Liautaud | 2/14 |
| 2,755,803 | 7/1956 | Dorsey | 2/426 |
| 2,918,676 | 12/1959 | Matheson | 2/440 |
| 3,027,562 | 4/1962 | Widenor | 2/430 |
| 3,584,939 | 6/1971 | Olson et al. | 351/132 |
| 3,993,403 | 11/1976 | Brown | 351/178 |
| 4,176,410 | 12/1979 | Matthias | 2/436 |
| 4,222,640 | 9/1980 | Bononi | 351/83 |
| 4,229,837 | 10/1980 | Solari | 2/439 |
| 4,279,040 | 7/1981 | Garofalo | 2/428 |
| 4,367,561 | 1/1983 | Solari | 2/439 |
| 4,688,272 | 8/1987 | Leonardi | 2/431 |
| 5,016,293 | 5/1991 | Lickle | 2/436 |
| 5,033,837 | 7/1991 | Leonardi | 351/121 |
| 5,042,094 | 8/1991 | Sadowsky | 2/454 |
| 5,046,198 | 9/1991 | Hunnebeck | 2/440 |
| 5,137,342 | 8/1992 | Jannard et al. | 351/123 |
| 5,138,723 | 8/1992 | Bollé | 2/430 |
| 5,184,354 | 2/1993 | Alfaro et al. | 2/425 |

FOREIGN PATENT DOCUMENTS

| | | | |
|---|---|---|---|
| 0496381 | 11/1919 | France | 2/431 |
| 1535556 | 7/1968 | France . | |
| 0506357 | 12/1954 | Italy | 2/431 |
| 215693 | 5/1924 | United Kingdom . | |
| 8600012 | 1/1986 | WIPO | 351/114 |

Primary Examiner—Peter Nerbun
Attorney, Agent, or Firm—Roylance, Abrams, Berdo & Goodman

[57] ABSTRACT

A sports pad for substantially covering certain exposed areas of an eyewear frame to prevent facial cutting from the hard, rigid eyewear frame. The sports pad is preferably formed of a resilient, flexible elastomeric material. The sports pad is removably coupled to the eyewear frame by stretching the sports pad relative the eyewear frame. Preferably, the sports pad includes a pair of temple cushions and a nose cushion.

17 Claims, 4 Drawing Sheets

SPORTS PAD FOR EYEWEAR FRAMES

FIELD OF THE INVENTION

This invention relates to sports pads for covering eyewear frames. More specifically, the invention relates to a soft, resilient pad for covering sports eyeglasses for use in sporting activities to prevent eye injury to a player from a ball, equipment, hands, or the like. The sports pad is removably coupled to the rigid frame of the eyeglasses for substantially covering the entire exposed area of the frame to prevent facial cutting.

BACKGROUND OF THE INVENTION

In a large number of sporting activities, such as tennis, hand ball, squash, racket ball, basketball, soccer, football, hockey, and other sporting activities in which there is fast movement of players and the use of a ball or other physical contact, there exists a continuing danger of a participant being struck in the eye by the ball, equipment or hand of an opponent. This can result in severe injury or even, in some cases, loss of an eye.

Thus, a variety of different types of protective eyewear has been developed for each of the variety of sporting activities. Generally, the protective eyewear are formed as either eyeglasses or goggles. Many of these prior protective eyeglasses suffer from one or more deficiencies. For example, some protective eyewear are very uncomfortable to wear since they are made of a very hard rigid plastic. Other protective eyewear is heavy and cumbersome to wear, which causes the wearer substantial discomfort during participation in the sporting event.

Accordingly, most protective eyewear is now constructed of lightweight, hard, rigid plastic with pads fixedly coupled thereto. For example, U.S. Pat. No. 4,688,272 to Leonardi discloses sports frames constructed of a lightweight plastic with a pair of temple pads and a nose pad fixedly coupled thereto. However, the sports frames disclosed by the Leonardi patent and many other prior eyeglasses do not provide easily removable pads which can be replaced when they wear out, or which can be changed with other pads of a different color to provide a different fashionable look.

Moreover, many prior eyeglasses do not provide sufficient pad to cover substantially all areas of the frame which are exposed to the wearer. Accordingly, the wearer of such eyeglasses is quite often cut by the frames, when the frames are struck by an object. Some eyeglasses have been manufactured with additional pads or padding in an attempt to overcome this problem. However, these eyeglasses present other problems or disadvantages. Namely, the padding often interferes with the installation of the lenses into the frame of the eyeglasses, since the optician cannot heat the frame without damaging the padding. Also, if the padding is molded onto the frame of the eyeglasses, then both the padding and frames are lost if either part is flawed and rejected.

Other examples of various prior devices relating to protective eyewear are disclosed in U.S. Pat. Nos. 1,288,140 to Nixson; 1,344,474 to Beattey; 1,754,694 to Neuwirth; 2,406,608 to Joyce; 2,504,524 to Hayward; 2,545,428 to Liautaud; 2,755,803 to Dorsey; 3,584,939 to Olson et al; 3,993,403 to Brown; 4,176,410 to Matthias; 4,222,640 to Bononi; 4,229,837 to Solari; 4,367,561 to Solari; 5,016,293 to Lickle; 5,033,837 to Leonardi; 5,046,198 to Hunnebeck; 5,137,342 to Jannard et al; 5,138,723 to Bolle and 5,184,354 to Alfaro et al.

In view of the above, it is apparent that there exists a need for protective eyewear which is comfortable to wear and can be used in almost any sporting activity. This invention addresses these needs in the art, along with other needs which will become apparent to those skilled in the art once given this disclosure.

SUMMARY OF THE INVENTION

Accordingly, an object of the invention is to provide a soft, resilient connector pad for covering portions of a rigid eyewear frame which are exposed to the wearer's face.

Another object of the invention is to provide a sports pad for eyeglasses which can be easily replaced.

Another further object of the invention is to provide a sports pad that is simple to manufacture, aesthetically pleasing, and not bulky.

Yet another object of the invention is to provide a pair of sports eyeglasses which are comfortable to wear.

The foregoing objects are basically obtained by providing a removable sports pad, comprising: a front portion having a first end and a second end with the front portion being shaped to removably overlie a portion of the eyewear frame; a first temple portion with a first temple cushion coupled thereto, the first temple portion being coupled to the first end of the front portion and shaped to removably overlie a first temple portion of the eyewear frame; and a second temple portion with a second temple cushion coupled thereto, the second temple portion being coupled to the second end of the front portion and shaped to removably overlie a second temple portion of the eyewear frame.

Other objects, advantages and salient features of the invention will become apparent from the following detailed description, which, taken in conjunction with the annexed drawings, discloses a preferred embodiment of the invention.

BRIEF DESCRIPTION OF THE DRAWINGS

Referring now to the drawings which form part of this original disclosure.

DETAILED DESCRIPTION OF THE INVENTION

Referring initially to FIGS. 1–4, a pair of sports eyeglasses 10 with a sports pad 12 coupled to a frame 14 is illustrated in accordance with the present invention. Sports pad 12 is removably coupled to frame 14, and constructed of a soft, flexible, resilient rubber material which allows pad 12 to be stretched over frame 14.

Pad 12 covers substantially all exposed areas of frame 14 which can cause facial cutting when the eyeglasses 10 are struck by an object. Accordingly, the soft, rubber material of pad 12 is preferably transversely compressible to compress between the wearer's head and eyeglasses upon the eyeglasses 10 being struck by an object. In other words, pad 12 will prevent facial cutting from the hard frame 14 of eyeglasses 10 by absorbing a portion of the force exerted on the wearer's head from an object striking eyeglasses 10.

Preferably, pad 12 is injection molded from a thermoplastic elastomer as a one-piece, unitary member, i.e., constructed of one substantially homogeneous piece of material, not including separate but joined elements. Frame 14, on the other hand, is constructed of a hard material, and includes a pair of lenses 16 and 18 fixedly coupled thereto.

As seen in FIGS. 1–4, pad 12 substantially covers and encompasses all exposed areas of frame 14 to prevent facial cutting from the hard frame 14 during impact with an object. A particularly suitable material for pad 12 is a very soft, elastomeric material with a durometer of approximately 13 ASTM A Shore to approximately 20 ASTM A Shore, such as the elastomer sold under the trademark Elastalloy which is an elastomeric derivative of the elastomer manufactured and sold by Shell Chemical Company under the trademark Kraton. Basically, the Elastalloy and Kraton elastomers are comprised of a block copolymer of butadiene, isoprene and styrene.

Pad 12 can be removably installed over frame 14 by stretching the resilient, rubber material of pad 12 over rigid frame 14 of eyeglasses 10. Accordingly, pad 12 can be easily replaced when worn out or changed to a different color pad. For example, pad 12 can be sold separately in a variety of colors, or sold as a kit containing a pair of protective eyeglasses 10 and a plurality of pads in a variety of colors.

Frame 14 is a conventional protective frame which is constructed of a hard, rigid material. It will be apparent to those skilled in the art from this disclosure that a variety of frames of other configurations can be used in conjunction with the present invention by modifying pad 12 to properly fit the particular configuration of the particular frames being used.

Figure 1:
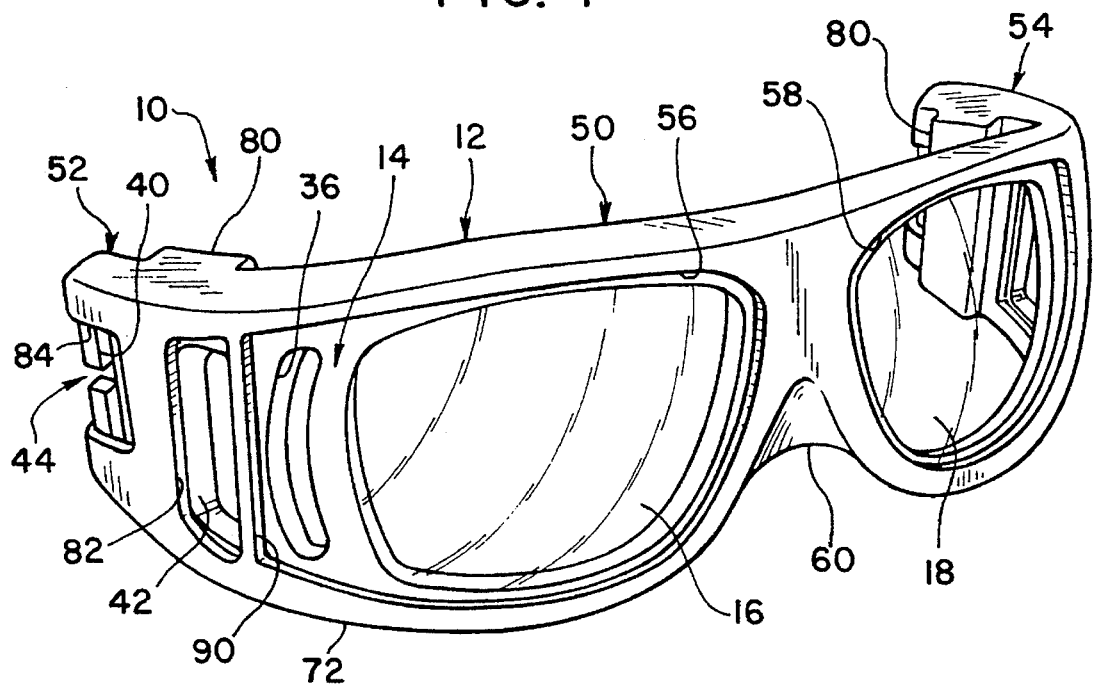
FIG. 1 is a front perspective view of a pair of conventional sports eyeglasses covered by a sports pad in accordance with the present invention.
Figure 2:
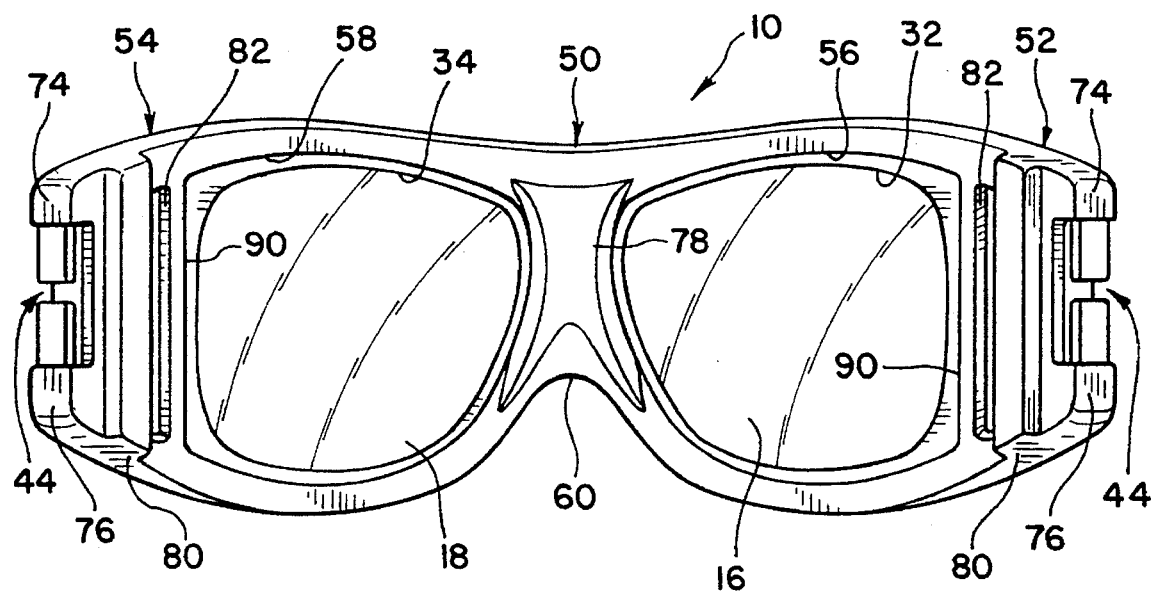
FIG. 2 is a rear elevational view of the eyeglasses and sports pad illustrated in FIG. 1 in accordance with the present invention.
Figure 3:
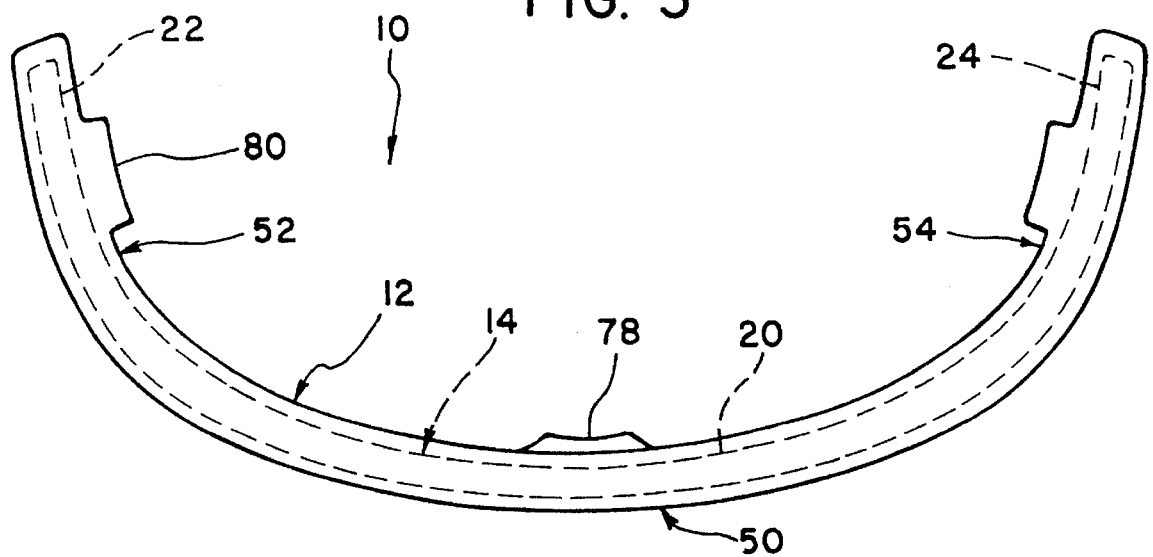
FIG. 3 is a top plan view of the eyeglasses and sports pad illustrated in FIGS. 1 and 2 in accordance with the present invention.
Figure 4:
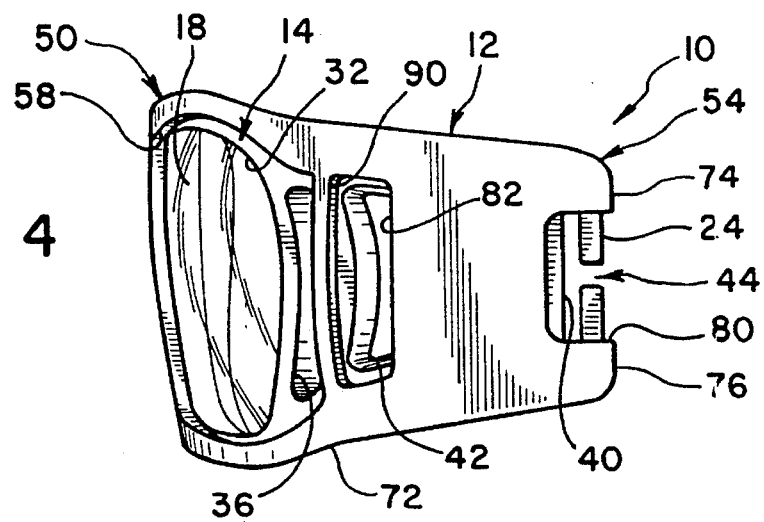
FIG. 4 is a side elevational view of the eyeglasses and sports pad illustrated in FIGS. 1–3.
Figure 5:
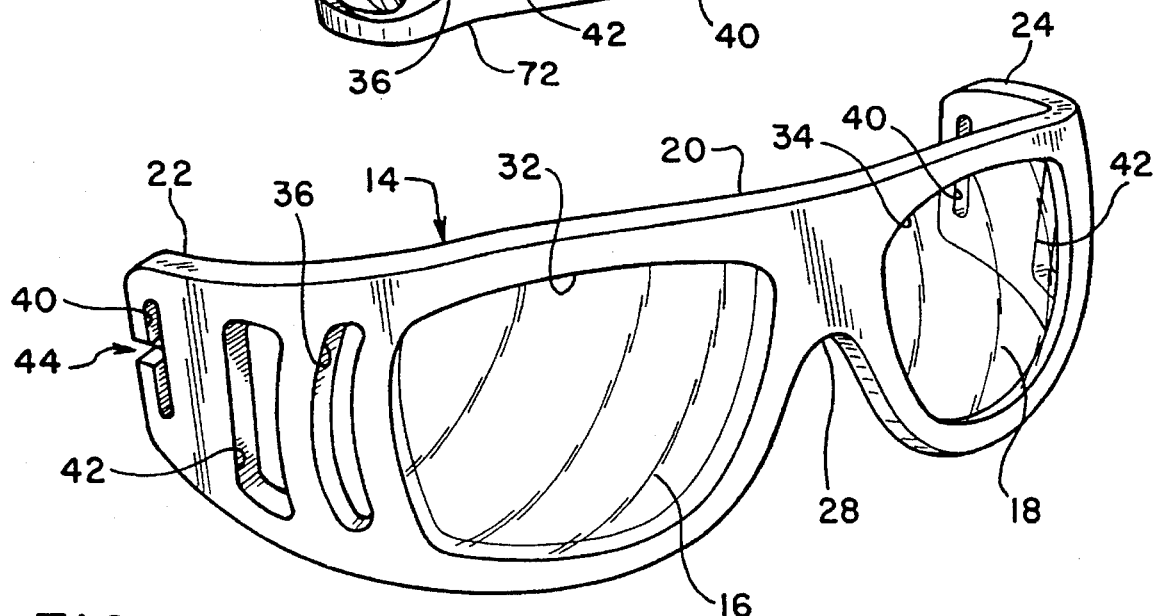
FIG. 5 is a front perspective view of the conventional prior art sports eyeglasses illustrated in FIGS. 1–4 with the sports pad removed.

As seen in FIG. 5, frame 14 is preferably integrally molded as a one-piece, unitary frame having a curved front portion 20, a first end or temple portion 22 extending rearwardly from one end of front portion 20, and a second end or temple portion 24 extending rearwardly from the other end of front portion 20. The integrally molded frame 14 can be constructed of any material, but is advantageously constructed of a lightweight, moldable, shatterproof polymeric material, such as polycarbonate, propionate, cellulose acetate, nylon or butyrate. Frame 14 is illustrated in the figures as being constructed of an opaque material which can be any color. However, it will be apparent from this disclosure that frame 14 can be constructed of a transparent material which is either clear or colored.

Front portion 20 of frame 14 includes a centrally located nose area 28 forming a curved recess for receiving a wearer's nose, and a pair of apertures 32 and 34 for retaining lenses 16 and 18 therein. In particular, each of the apertures 32 and 34 preferably has a peripheral recess for retaining lenses 16 and 18, respectively, therein. Lenses 16 and 18 can be either refractive, i.e., prescription lenses, or non-refractive, i.e., non-prescription lenses, as needed. Of course, when using non-prescription lenses, lenses 16 and 18 can be integrally formed with frame 14 as a one-piece, unitary member with frame 14 and lenses 16 and 18 being formed of a clear or colored transparent plastic material. Alternatively, apertures 32 and 34 can be interconnected for receiving a single lens which is either refractive or non-refractive.

Optionally, front portion 20 of frame 14 can have a pair of ventilation openings 36 and 38 to provide adequate circulation of air between frame 14 and the wearer's face. In particular, ventilation opening 36 is positioned between first end portion 22 and aperture 32, and ventilation opening 38 is positioned between second end portion 24 and aperture 34.

As particularly seen in FIG. 5, first end portion 22 and second end portion 24 are integrally molded with front portion 20 and extends approximately 1.5 inches rearwardly from the ends of front portion 20. First end or temple portion 22 and second end or temple portion 24 are substantially identical, and thus, only first end portion 22 will be discussed and illustrated in detail.

First end portion 22 has a strap slot 40 at its free end and an optional ventilation opening 42 at its other end. The forward edge of ventilation opening 42 demarks the transition point between frame front 20 and first end portion 22. Ventilation opening 42 also ensures adequate circulation of air between the wearer's face and frame 14 of the eyeglasses 10 with pad 12 thereon.

Strap slot 40 extends substantially vertically when eyeglasses 10 are worn by a wearer, and receives a conventional headband or strap (not shown) for securing the eyeglasses 10 to the wearer's head. An access slot 44 extends substantially perpendicularly from the midpoint of strap slot 40 to the free end of first end portion 22 to provide easy installation of the headband or strap (not shown) into strap slot 40 in a conventional manner.

Referring now to FIGS. 8–11, pad 12 is constructed as a one-piece, unitary member, and includes a front portion 50 for overlying and encompassing substantially all of the exposed areas of front portion 20 of frame 14, and first and second end or temple portions 52 and 54 for substantially overlying and encompassing all of the exposed areas of end portions 22 and 24 of frame 14, respectively. Accordingly, pad 12 fits over the hard, rigid material of frame 14 to provide a cushioning effect on the top, bottom, front and rear sides of frame 14 by substantially covering all of the exposed surfaces of frame 14.

Pad 12 is dimensioned smaller than frame 14 so that pad 12 can be installed and removed by stretching pad 12 onto frame 14. The stretchability and resiliency of pad 12 permits a single pad 12 to be used on a plurality of different sizes of frames. In other words, a plurality of sizes of frames 14 can be fitted with the same pad 12 formed from a single mold due to the large degree of elasticity of pad 12.

Front portion 50 of pad 12 includes a pair of lens apertures 56 and 58, and a nose portion 60 positioned between lens apertures 56 and 58. Apertures 56 and 58, in their normal unstretched state, are preferably non-uniformly smaller than apertures 32 and 34 of frame 14 to provide a secure fit about the frame 14. In particular, apertures 56 and 58 each has an upper concaved portion 62 and a lower concaved portion 64 for engaging and gripping the portion of frame 14 about apertures 32 and 34 of frame 14. The non-uniformity of front portion 50 of pad 12 depends upon the size and shape of frame 14. In other words, the precise shape of pad 12 will vary depending upon the shape of frame 14.

Figure 10:
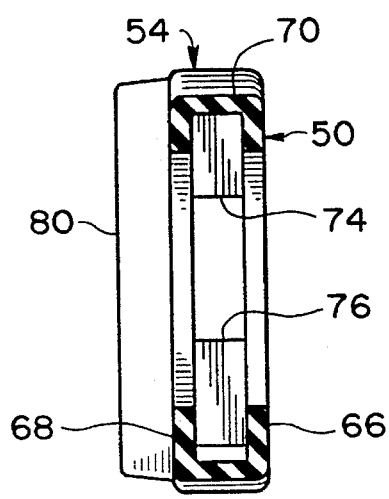
FIG. 10 is a cross-sectional view of the unstretched sports pad of FIGS. 1–4 and 6–9 taken along section line 10—10 of FIG. 9.
Figure 11:
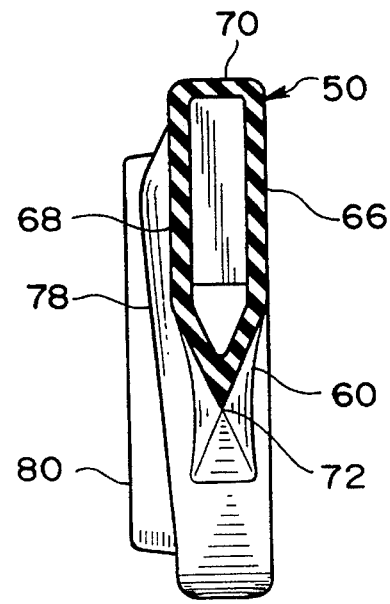
FIG. 11 is a cross-sectional view of the unstretched sports pad of FIGS. 1–4 and 6–10 taken along section line 11—11 of FIG. 9.

As seen in FIGS. 10 and 11, front portion 50 of pad 12 is formed by a front wall 66, a rear wall 68, a top peripheral wall 70 and a bottom peripheral wall 72. Front wall 66, rear wall 68, top peripheral wall 70 and bottom peripheral wall 72 extend from front portion 50 to form part of end portions 52 and 54. End portions 52 and 54 also include a pair of end walls 74 and 76 which together with front wall 66, rear wall 68, top wall 70 and bottom wall 72 form a pair of end pockets for engaging end portions 22 and 24 of frame 14. These end pockets of pad 12 are stretched over end portions 22 and 24 to place pad 12 under longitudinal tension as well as transverse tension. Accordingly, pad 12 is elastically stretched and thereby retained on frame 14 to limit shifting of pad 12 on frame 14.

Figure 8:
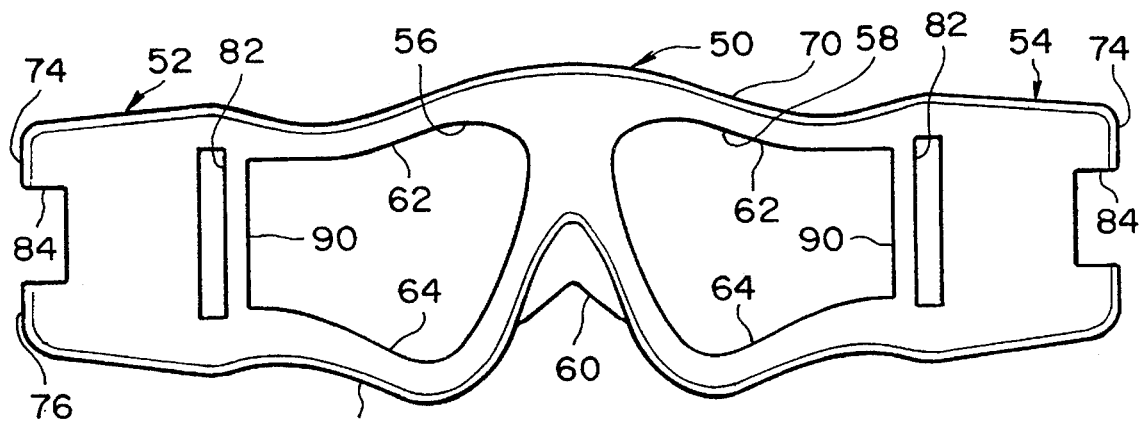
FIG. 8 is a front elevational view of the sports pad illustrated in FIGS. 1–4, 6 and 7 in its original unstretched state.
Figure 9:
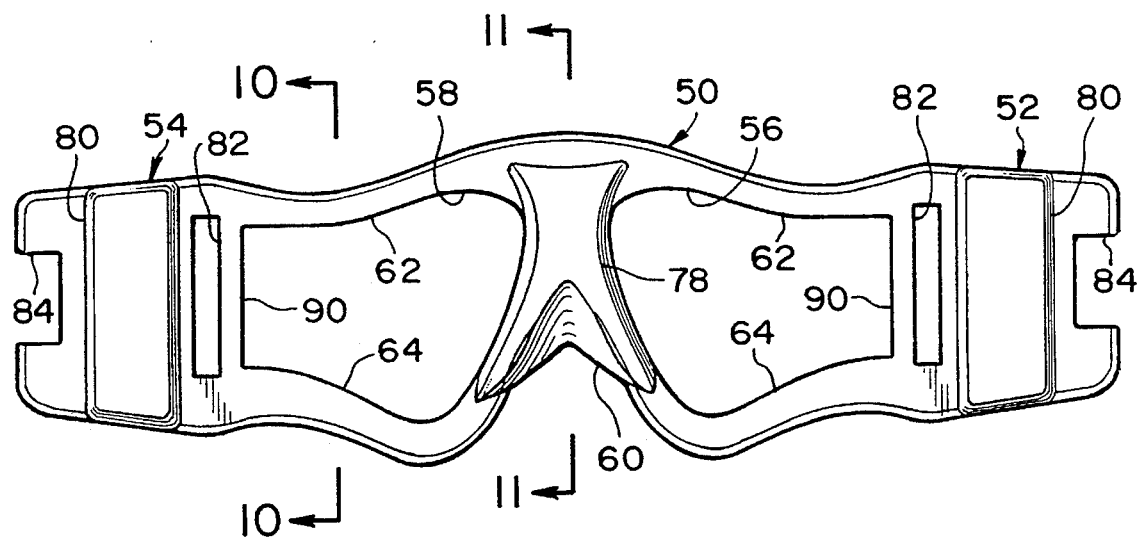
FIG. 9 is a rear elevational view of the sports pad illustrated in FIGS. 1–4 and 6–8 in its original unstretched state.

When pad 12 is in its unstressed state as shown in FIGS. 8 and 9, front wall 66 is parallel to and spaced from rear wall 68 to receive frame 14 therebetween. Preferably, the distance between front wall 66 and rear wall 68 is slightly greater than the thickness of frame 14 in its unstressed state. Of course, the distance between front wall 66 and rear wall 68 can be smaller than or the same size as the thickness of frame 14. Preferably, when pad 12 is stretched onto frame 14, the distance between rear front wall 66 and rear wall 68 will decrease to elastomerically grip frame 14.

Top peripheral wall 70 and bottom peripheral wall 72 extend substantially perpendicularly between front wall 66 and rear wall 68 for engaging the upper and lower edges of frame 14, respectively. End walls 74 and 76, together with front wall 66, rear wall 68, top peripheral wall 70 and bottom peripheral wall 72 of end portions 52 and 54, form a pair of end pockets for engaging the ends of frame 14. Walls 66, 68, 70, 72, 74 and 76 preferably have a thickness ranging from about 0.075 inch to about 0.090 inch.

Nose portion 60 includes a nose cushion 78 which extends outwardly from rear wall 68 between apertures 56 and 58. Nose cushion 78 provides additional padding between the wearer's nose and the nose area 28 of frame 14. In particular, nose cushion 78 is contoured to engage the wearer's nose and has a variable thickness ranging from about 0.075 inch to about 0.220 inch. Of course, nose cushion 78 can be made thicker or smaller as needed or desired.

First and second end or temple portions 52 and 54 are substantially identical, and thus, only first end or temple portion 52 will be discussed herein. First end or temple portion 52 includes a temple cushion 80, a ventilation opening 82 positioned between temple cushion 80 and aperture 56 of pad 12, and a cutout 84 for exposing strap slot 40 and access slot 44 to accommodate a headband or strap (not shown) therein.

Temple cushion 80 extends outwardly from rear wall 68 of pad 12 for engaging the wearer's temple. Preferably, temple cushion 80 extends outwardly from rear wall 68 by a distance approximately 0.490 inch.

Pad 12 has four bars 90 with one of the bars 90 being located between each of the ventilation openings 82 and the apertures 56 and 58 of the pad. Optionally, pad 12 may be constructed without some or all of the ventilation openings 82. For example, the two bars 90 on rear wall 68 of pad 12 may be removed so that apertures 56 and 58 of the rear wall are larger than apertures 56 and 58 of the front wall 66 of pad 12. In other words, apertures 56 and 58 of the rear wall 68 would encompass ventilation openings 82 when the two bars 90 on the rear wall 68 are removed.

Ventilation openings 82 are sized and positioned to coincide with ventilation openings 42 of frame 14 when pad 12 is coupled to frame 14. Accordingly, this arrangement allows for adequate ventilation between the eyeglasses 10 and the wearer without exposing the hard plastic to the wearer's face. In other words, pad 12 provides adequate cushioning between the wearer's face and eyeglasses 10 without blocking the ventilation opening 42 of frame 14.

ASSEMBLY

Figure 6:
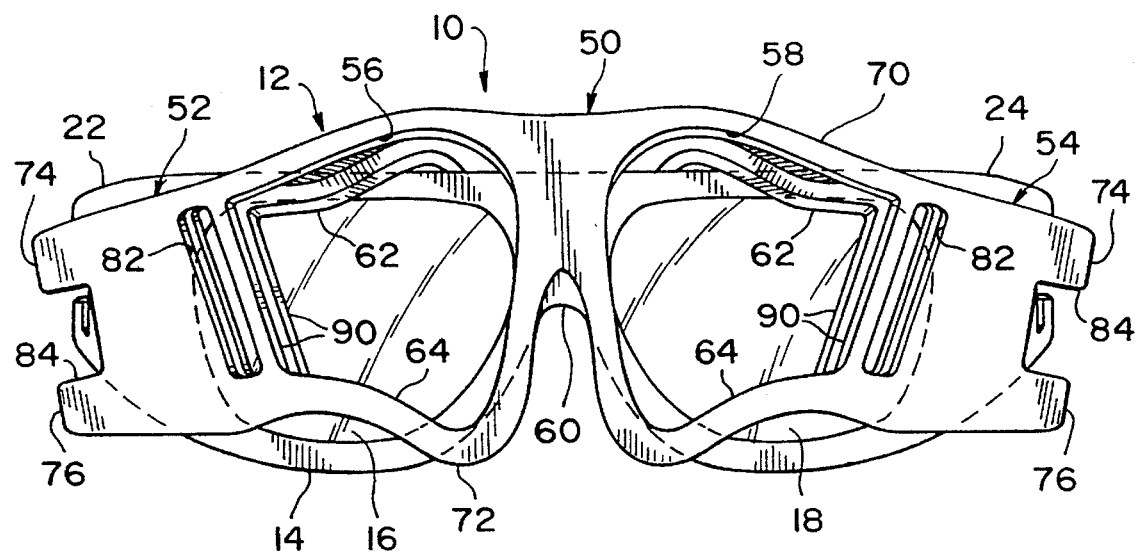
FIG. 6 is a front elevational view of the sports pad illustrated in FIGS. 1–4 with the sports pad partially covering the conventional prior art sports eyeglasses of FIG. 5.
Figure 7:
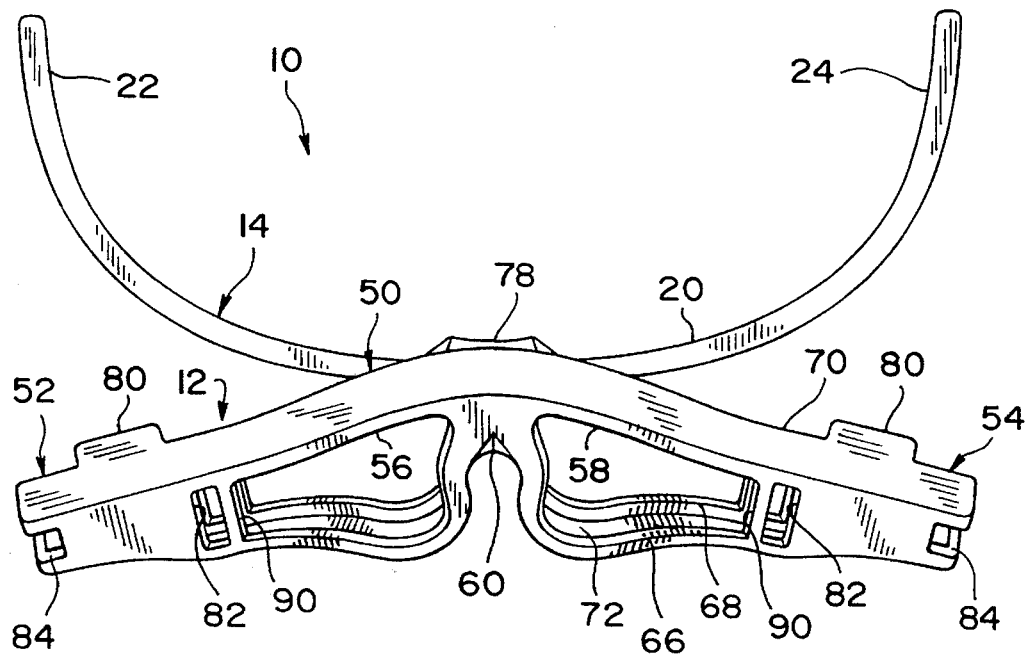
FIG. 7 is a top plan view of the sports pad and the conventional prior art sports eyeglasses illustrated in FIG. 6 with the sports pad partially covering the sports eyeglasses.

Pad 12 can be easily installed onto an existing frame such as frame 14 by stretching pad 12 over frame 14. In particular, the nose portion 60 of pad 12 is stretched, and one of the end portions 22 or 24 of frame 14 is then inserted in between front wall 66 and rear wall 68 of nose portion 60, until nose portion 60 of pad 12 rests in nose area 28 of frame 14 as shown in FIGS. 6 and 7. Since pad 12 is constructed of a resilient elastomeric material, nose portion 60 of pad 12 will snugly and firmly grip nose area 28 of frame 14.

Now, one of the end portions 52 or 54 is stretched longitudinally and slipped over the corresponding end portion 22 or 24 of frame 14 to position end portion 22 or 24 between front wall 66 and rear wall 68 of either end portion 52 or 54 of pad 12. Next, the other of the end portion 52 or 54 is likewise stretched longitudinally and slipped over the corresponding end portion 22 or 24 of frame 14 to position end portion 22 or 24 between front wall 66 and rear wall 68 of pad 12. Finally, pad 12 can now be moved and adjusted to correctly position pad 12 on frame 14.

If the pad 12 becomes worn out, or if it is desired to change the color of the pad 12, then the wearer need only reverse the assembly steps set forth above to remove pad 12 from frame 14. Of course, since pad 12 is very resilient, it is possible to assemble pad 12 onto frame 14 in a variety of ways by stretch pad 12 over frame 14.

While only one embodiment has been chosen to illustrate the invention, it will be understood by those skilled in the art that various changes and modifications can be made herein without departing from the scope of the invention as defined in the appended claims.

What is claimed is:

1. A removable sports pad for covering certain exposed areas of an eyewear frame, comprising:

a front portion having a front wall, a rear wall spaced from said front wall, a top peripheral wall extending between said front wall and said rear wall and a bottom peripheral wall extending between said front wall and said rear wall for forming a channel to receive the eyewear frame therebetween, each of said front and rear walls having a pair of lens apertures with a nose portion formed therebetween and interconnecting said top and bottom peripheral walls, said front portion being shaped to removably overlie a portion of the eyewear frame adapted to be received within said channel;

a first temple portion with a first temple cushion coupled thereto, said first temple portion being coupled to one end of said front portion and shaped to removably overlie a first temple portion of the eyewear frame; and a second temple portion with a second temple cushion coupled thereto, said second temple portion being coupled to an opposite end of said front portion and shaped to removably overlie a second temple portion of the eyewear frame;

said front portion of said pad and said first and second temple portions of said pad being integrally formed as a one-piece, unitary member from a soft, stretchable, resilient material.

2. A removable sports pad according to claim 1, wherein said front portion of said pad further includes an outwardly extending nose cushion formed on said nose portion of said rear wall.

3. A removable sports pad according to claim 1, wherein said first temple portion of said pad further includes a rear wall with said first temple cushion coupled thereto, a front wall spaced from said rear wall of said first temple portion of said pad, a top peripheral wall extending between said front and rear walls of said first temple portion of said pad, and a bottom peripheral wall extending between said front and rear walls of said first temple portion of said pad.

4. A removable sports pad according to claim 3, wherein said second temple portion of said pad further includes a rear wall with said second temple cushion coupled thereto, a front wall spaced from said rear wall of said second temple portion of said pad, a top peripheral wall extending between said front and rear walls of said second temple portion of said pad, and a bottom peripheral wall extending between said front and rear walls of said second temple portion of said pad.

5. A removable sports pad according to claim 4, wherein said rear walls of said first and second temple portions of said pad extend substantially continuously with said rear wall of said front portion of said pad.

6. A removable sports pad according to claim 5, wherein said front walls of said first and second temple portions of said pad extend substantially continuously with said front wall of said front portion of said pad.

7. A removable sports pad according to claim 6, wherein said top and bottom peripheral walls of said first and second temple portions of said pad extend substantially continuously with said top and bottom peripheral walls of said front portion of said pad.

8. A removable sports pad according to claim 4, wherein each of said first and second temple portions of said pad includes an end peripheral wall extending transverse to said top peripheral wall, said rear wall and said front wall of said first and second temple portions of said pad, respectively.

9. A removable sports pad for covering at least certain inwardly facing areas of an eyewear frame, comprising:

a soft, stretchable rear wall being stretchably shaped to overlie inwardly facing areas of the eyewear frame, said rear wall including a front portion having a pair of lens apertures with a nose portion located therebetween for overlying inwardly facing portions of a front portion of the eyewear frame, a first temple portion integrally formed as a one-piece, unitary member with a first end of said front portion of said rear wall for overlying an inwardly facing portion of a first temple portion of the eyewear frame, and a second temple portion integrally formed as a one-piece, unitary member with a second end of said front portion of said rear wall for overlying an inwardly facing portion of a second temple portion of the eyewear frame; and coupling means, coupled to said rear wall, for removably securing said rear wall to the eyewear frames by stretching said rear wall to overlie the inwardly facing portions of the eyewear frame, said coupling means including a front wall having a pair of lens apertures with a nose portion located therebetween and integrally formed as a one-piece, unitary member with said rear wall, and top and bottom peripheral walls integrally formed as a one-piece unitary member with said rear wall and said front wall to form a channel adapted to receive the eyewear frame therein, said nose portions of said front and rear walls interconnecting said top and bottom peripheral walls.

10. A removable sports pad according to claim 7, wherein each of said first and second temple portions of said pad includes a temple cushion.

11. A removable sports pad according to claim 10, wherein said front portion of said pad further includes an outwardly extending nose cushion formed on said nose portion of said rear wall.

12. A removable sports pad according to claim 9, wherein said front, rear, top and bottom walls are adapted to substantially cover all exposed areas of the eyewear frame.

13. Sports eyewear for eye protection, comprising:

a substantially rigid eyewear frame having a front portion with at least one lens coupled thereto, a first temple portion being coupled to a first end of said front portion of said frame, and a second temple portion being coupled to a second end of said front portion of said frame; and a soft, stretchable, elastomeric pad removably coupled to said frame for covering certain exposed areas of said frame, said pad including a front portion having a front wall, a rear wall spaced from said front wall, a top peripheral wall extending between said front wall and said rear wall and a bottom peripheral wall extending between said front wall and said rear wall for forming a channel to receive the eyewear frame therebetween, each of said front and rear walls having a pair of lens apertures with a nose portion formed therebetween which interconnects said top and bottom peripheral walls, said front portion of said pad being shaped to removably overlie said front portion of said frame;

a first temple portion integrally formed as a one-piece, unitary member with said front portion of said pad and shaped to removably overlie said first temple portion of said frame; and a second temple portion integrally formed as a one-piece, unitary member with said pad being coupled to said second end of said front portion of said pad and shaped to removably overlie said second temple portion of said frame.

14. Sports eyewear according to claim 13, wherein said front portion of said frame is integrally formed with said first and second temple portions of said frame as a unitary, one-piece member.

15. Sports eyewear according to claim 13, wherein said front portion of said pad further includes an outwardly extending nose cushion formed on said nose portion of said rear wall.

16. Sports eyewear according to claim 13, wherein said first temple portion of said pad further includes a rear wall with said first temple cushion coupled thereto, a front wall spaced from said rear wall of said first temple portion of said pad, a top peripheral wall extending between said front and rear walls of said first temple portion of said pad, and a bottom peripheral wall extending between said front and rear walls of said first temple portion of said pad; and said second temple portion of said pad further includes a rear wall with said second temple cushion coupled thereto, a front wall spaced from said rear wall of said second temple portion of said pad, a top peripheral wall extending between said front and rear walls of said second temple portion of said pad, and a bottom peripheral wall extending between said front and rear walls of said second temple portion of said pad.

17. Sports eyewear according to claim 16, wherein said rear walls of said first and second temple portions of said pad extend substantially continuously with said rear wall of said front portion of said pad;

said front walls of said first and second temple portions of said pad extend substantially continuously with said front wall of said front portion of said pad; and said top and bottom peripheral walls of said first and second temple portions of said pad extend substantially continuously with said top and bottom peripheral walls of said front portion of said pad.

* * * * *